(12) United States Patent
Markov et al.

(10) Patent No.: US 10,878,573 B2
(45) Date of Patent: *Dec. 29, 2020

(54) SYSTEM AND METHOD FOR SEGMENTATION OF LUNG

(71) Applicant: COVIDIEN LP, Mansfield, MA (US)

(72) Inventors: Igor A. Markov, Hod Hasharon (IL); Yuri Kreinin, Aurora (CA)

(73) Assignee: COVIDIEN LP, Mansfield, MA (US)

( * ) Notice: Subject to any disclaimer, the term of this patent is extended or adjusted under 35 U.S.C. 154(b) by 91 days.

This patent is subject to a terminal disclaimer.

(21) Appl. No.: 16/124,371

(22) Filed: Sep. 7, 2018

(65) Prior Publication Data

US 2019/0019294 A1 Jan. 17, 2019

Related U.S. Application Data

(63) Continuation of application No. 15/808,975, filed on Nov. 10, 2017, now Pat. No. 10,074,185, which is a
(Continued)

(51) Int. Cl.
*G06K 9/00* (2006.01)
*G06T 7/13* (2017.01)
(Continued)

(52) U.S. Cl.
CPC ............... *G06T 7/13* (2017.01); *G06T 7/0012* (2013.01); *G06T 7/11* (2017.01); *G06T 7/136* (2017.01);
(Continued)

(58) Field of Classification Search
None
See application file for complete search history.

(56) References Cited

U.S. PATENT DOCUMENTS 5,592,939 A 1/1997 Martinelli
5,611,025 A 3/1997 Lorensen et al.
(Continued)

FOREIGN PATENT DOCUMENTS

KR 2007-0085120 A 8/2007
KR 2011-0018573 A 2/2011
WO 2008017984 A2 2/2008

OTHER PUBLICATIONS

Australian Examination Report issued in corresponding Appl. No. AU 2015284218 dated Mar. 7, 2019 (3 pages).
(Continued)

*Primary Examiner* — Atiba O Fitzpatrick

(57) ABSTRACT

Disclosed are systems, devices, and methods for determining pleura boundaries of a lung, an exemplary method comprising acquiring image data from an imaging device, generating a set of two-dimensional (2D) slice images based on the acquired image data, determining, by a processor, a seed voxel in a first slice image from the set of 2D slice images, applying, by the processor, a region growing process to the first slice image from the set of 2D slice images starting with the seed voxel using a threshold value, generating, by the processor, a set of binarized 2D slice images based on the region grown from the seed voxel, filtering out, by the processor, connected components of the lung in each slice image of the set of binarized 2D slice images, and identifying, by the processor, the pleural boundaries of the lung based on the set of binarized 2D slice images.

13 Claims, 9 Drawing Sheets

Related U.S. Application Data continuation of application No. 14/754,867, filed on Jun. 30, 2015, now Pat. No. 9,836,848.

(60) Provisional application No. 62/020,261, filed on Jul. 2, 2014.

(51) Int. Cl.

| | | |
|---|---|---|
| *G06T 7/11* | (2017.01) | |
| *G06T 7/187* | (2017.01) | |
| *G06T 7/00* | (2017.01) | |
| *G06T 7/155* | (2017.01) | |
| *G06T 7/136* | (2017.01) | |
| *G06F 19/00* | (2018.01) | |
| *G16H 30/20* | (2018.01) | |
| *G16H 30/40* | (2018.01) | |

(52) U.S. Cl.
CPC .............. *G06T 7/155* (2017.01); *G06T 7/187* (2017.01); *G06F 19/321* (2013.01); *G06T 2207/10081* (2013.01); *G06T 2207/20101* (2013.01); *G06T 2207/20156* (2013.01); *G06T 2207/30061* (2013.01); *G16H 30/20* (2018.01); *G16H 30/40* (2018.01)

(56) References Cited

U.S. PATENT DOCUMENTS

| | | |
|---|---|---|
| 5,676,673 A | 10/1997 | Ferre et al. |
| 5,697,377 A | 12/1997 | Wittkampf |
| 5,699,799 A | 12/1997 | Xu et al. |
| 5,715,836 A | 2/1998 | Kliegis et al. |
| 5,729,129 A | 3/1998 | Acker |
| 5,752,513 A | 5/1998 | Acker et al. |
| 5,782,762 A | 7/1998 | Vining |
| 5,881,124 A | 3/1999 | Giger et al. |
| 5,891,030 A | 4/1999 | Johnson et al. |
| 5,913,820 A | 6/1999 | Bladen et al. |
| 5,920,319 A | 7/1999 | Vining et al. |
| 5,967,980 A | 10/1999 | Ferre et al. |
| 5,971,767 A | 10/1999 | Kaufman et al. |
| 5,987,960 A | 11/1999 | Messner et al. |
| 6,019,725 A | 2/2000 | Vesely et al. |
| 6,047,080 A | 4/2000 | Chen et al. |
| 6,083,162 A | 7/2000 | Vining |
| 6,138,045 A | 10/2000 | Kupinski et al. |
| 6,151,404 A | 11/2000 | Pieper |
| 6,167,296 A | 12/2000 | Shahidi |
| 6,181,348 B1 | 1/2001 | Geiger |
| 6,201,387 B1 | 3/2001 | Govari |
| 6,233,476 B1 | 5/2001 | Strommer et al. |
| 6,246,784 B1 | 6/2001 | Summers et al. |
| 6,266,551 B1 | 7/2001 | Osadchy et al. |
| 6,332,089 B1 | 12/2001 | Acker et al. |
| 6,346,940 B1 | 2/2002 | Fukunaga |
| 6,366,800 B1 | 4/2002 | Vining et al. |
| 6,381,485 B1 | 4/2002 | Hunter et al. |
| 6,387,092 B1 | 5/2002 | Burnside et al. |
| 6,466,815 B1 | 10/2002 | Saito |
| 6,496,188 B1 | 12/2002 | Deschamps et al. |
| 6,501,848 B1 | 12/2002 | Carroll et al. |
| 6,501,981 B1 | 12/2002 | Schweikard et al. |
| 6,505,065 B1 | 1/2003 | Yanof et al. |
| 6,522,907 B1 | 2/2003 | Bladen et al. |
| 6,526,162 B2 | 2/2003 | Asano et al. |
| 6,535,756 B1 | 3/2003 | Simon et al. |
| 6,578,579 B2 | 6/2003 | Burnside et al. |
| 6,584,174 B2 | 6/2003 | Schubert et al. |
| 6,603,868 B1 | 8/2003 | Ludwig et al. |
| 6,611,793 B1 | 8/2003 | Burnside et al. |
| 6,650,927 B1 | 11/2003 | Keidar |
| 6,651,669 B1 | 11/2003 | Burnside |
| 6,694,163 B1 | 2/2004 | Vining |
| 6,757,557 B1 | 6/2004 | Bladen et al. |
| 6,783,523 B2 | 8/2004 | Qin et al. |
| 6,792,390 B1 | 9/2004 | Burnside et al. |
| 6,829,379 B1 | 12/2004 | Knoplioch et al. |
| 6,850,794 B2 | 2/2005 | Shahidi |
| 6,892,090 B2 | 5/2005 | Verard et al. |
| 6,898,263 B2 | 5/2005 | Avinash et al. |
| 6,909,913 B2 | 6/2005 | Vining |
| 6,920,347 B2 | 7/2005 | Simon et al. |
| 6,925,200 B2 | 8/2005 | Wood et al. |
| 7,006,677 B2 | 2/2006 | Manjeshwar et al. |
| 7,072,501 B2 | 7/2006 | Wood et al. |
| 7,085,400 B1 | 8/2006 | Holsing et al. |
| 7,096,148 B2 | 8/2006 | Anderson et al. |
| 7,149,564 B2 | 12/2006 | Vining et al. |
| 7,167,180 B1 | 1/2007 | Shibolet |
| 7,174,202 B2 | 2/2007 | Bladen et al. |
| 7,179,220 B2 | 2/2007 | Kukuk |
| 7,236,558 B2 | 6/2007 | Saito et al. |
| 7,301,332 B2 | 11/2007 | Govari et al. |
| 7,315,639 B2 | 1/2008 | Kuhnigk |
| 7,324,104 B1 | 1/2008 | Bitter et al. |
| 7,336,809 B2 | 2/2008 | Zeng et al. |
| 7,397,937 B2 | 7/2008 | Schneider et al. |
| 7,428,334 B2 | 9/2008 | Schoisswohl et al. |
| 7,452,357 B2 | 11/2008 | Vlegele et al. |
| 7,505,809 B2 | 3/2009 | Strommer et al. |
| 7,517,320 B2 | 4/2009 | Wibowo et al. |
| 7,518,619 B2 | 4/2009 | Stoval, III et al. |
| 7,630,752 B2 | 12/2009 | Viswanathan |
| 7,630,753 B2 | 12/2009 | Simon |
| 7,659,912 B2 | 2/2010 | Akimoto et al. |
| 7,702,153 B2 | 4/2010 | Hong et al. |
| 7,751,865 B2 | 7/2010 | Jascob et al. |
| 7,756,316 B2 | 7/2010 | Odry et al. |
| 7,788,060 B2 | 8/2010 | Schneider |
| 7,792,565 B2 | 9/2010 | Vining |
| 7,805,269 B2 | 9/2010 | Glossop |
| 7,809,176 B2 | 10/2010 | Gundel |
| 7,811,294 B2 | 10/2010 | Strommer et al. |
| 7,822,461 B2 | 10/2010 | Geiger et al. |
| 7,901,348 B2 | 3/2011 | Soper et al. |
| 7,907,772 B2 | 3/2011 | Wang et al. |
| 7,929,014 B2 | 4/2011 | Akimoto et al. |
| 7,951,070 B2 | 5/2011 | Ozaki et al. |
| 7,969,142 B2 | 6/2011 | Krueger et al. |
| 7,985,187 B2 | 7/2011 | Wibowo et al. |
| 8,009,891 B2 | 8/2011 | de Vaan |
| 8,049,777 B2 | 11/2011 | Akimoto et al. |
| 8,055,323 B2 | 11/2011 | Sawyer |
| 8,102,416 B2 | 1/2012 | Ito et al. |
| 8,126,241 B2 | 2/2012 | Zarkh et al. |
| 8,131,344 B2 | 3/2012 | Strommer et al. |
| 8,170,328 B2 | 5/2012 | Masumoto et al. |
| 8,199,981 B2 | 6/2012 | Koptenko et al. |
| 8,200,314 B2 | 6/2012 | Bladen et al. |
| 8,202,213 B2 | 6/2012 | Ito et al. |
| 8,208,708 B2 | 6/2012 | Homan et al. |
| 8,219,179 B2 | 7/2012 | Ganatra et al. |
| 8,257,346 B2 | 9/2012 | Qin et al. |
| 8,267,927 B2 | 9/2012 | Dalal et al. |
| 8,290,228 B2 | 10/2012 | Cohen et al. |
| 8,298,135 B2 | 10/2012 | Ito et al. |
| 8,385,688 B2 | 2/2013 | Gong et al. |
| 8,391,952 B2 | 3/2013 | Anderson |
| 8,417,009 B2 | 4/2013 | Mizuno |
| 8,494,612 B2 | 7/2013 | Vetter et al. |
| 8,509,877 B2 | 8/2013 | Mori et al. |
| 8,672,836 B2 | 3/2014 | Higgins et al. |
| 8,682,045 B2 | 3/2014 | Vining et al. |
| 8,696,549 B2 | 4/2014 | Holsing et al. |
| 8,698,806 B2 | 4/2014 | Kunert et al. |
| 8,700,132 B2 | 4/2014 | Ganatra et al. |
| 8,706,193 B2 | 4/2014 | Govari et al. |
| 8,709,034 B2 | 4/2014 | Keast et al. |
| 8,730,237 B2 | 5/2014 | Ruijters et al. |
| 8,768,029 B2 | 7/2014 | Helm et al. |
| 8,784,400 B2 | 7/2014 | Roschak |
| 8,798,227 B2 | 8/2014 | Tsukagoshi et al. |
| 8,798,339 B2 | 8/2014 | Mielekamp et al. |

(56) References Cited

U.S. PATENT DOCUMENTS

| | | | |
|---|---|---|---|
| 8,801,601 | B2 | 8/2014 | Prisco et al. |
| 8,819,591 | B2 | 8/2014 | Wang et al. |
| 8,862,204 | B2 | 10/2014 | Sobe et al. |
| 9,836,848 | B2 | 12/2017 | Markov et al. |
| 10,074,185 | B2 | 9/2018 | Markov et al. |
| 2002/0009215 | A1 | 1/2002 | Armato, III |
| 2003/0095692 | A1 | 5/2003 | Mundy et al. |
| 2003/0099385 | A1* | 5/2003 | Zeng ............... G06T 7/0012 382/128 |
| 2005/0001832 | A1 | 1/2005 | Shen |
| 2005/0286750 | A1* | 12/2005 | Dehmeshki ....... G06K 9/4638 382/131 |
| 2007/0127802 | A1* | 6/2007 | Odry ................. G06T 7/12 382/131 |
| 2007/0249931 | A1* | 10/2007 | Fain .............. G01R 33/56341 600/420 |
| 2008/0183073 | A1 | 7/2008 | Higgins et al. |
| 2009/0012390 | A1 | 1/2009 | Pescatore et al. |
| 2009/0030306 | A1 | 1/2009 | Miyoshi et al. |
| 2010/0128940 | A1 | 5/2010 | Buelow et al. |
| 2010/0235352 | A1 | 9/2010 | Slutsky et al. |
| 2010/0310146 | A1 | 12/2010 | Higgins et al. |
| 2010/0312094 | A1 | 12/2010 | Guttman et al. |
| 2011/0237897 | A1 | 9/2011 | Gilboa |
| 2011/0251607 | A1 | 10/2011 | Kruecker et al. |
| 2012/0203065 | A1 | 8/2012 | Higgins et al. |
| 2012/0249546 | A1 | 10/2012 | Tschirren et al. |
| 2012/0280135 | A1 | 11/2012 | Bal |
| 2012/0287238 | A1 | 11/2012 | Onishi et al. |
| 2013/0165854 | A1 | 6/2013 | Sandhu et al. |

OTHER PUBLICATIONS

Extended European Search report for application No. 15814448.5 dated Dec. 6, 2017 (7 pages).

Brown et al., Method for Segmenting Chest CT Image Data Using an Anatomical Model: Preliminary Rreults, IEEE Transactiosn on Medical Imaging, vol. 16, No. 6, Dec. 1, 1997, pp. 828-839.

Japanese Office Action issued in Appl. No. JP 2016-575072 dated Nov. 5, 2018, together with English language translation (8 pages).

PCT Search Report for International Patent Application No. PCT/US2015/038541, dated Oct. 13, 2015 (4 pages).

* cited by examiner

SYSTEM AND METHOD FOR SEGMENTATION OF LUNG

CROSS REFERENCE TO RELATED APPLICATIONS

The present application is a continuation of U.S. patent application Ser. No. 15/808,975, filed on Nov. 10, 2017, which is a continuation of U.S. patent application Ser. No. 14/754,867, now U.S. Patent No. 9,836,848, filed on Jun. 30, 2015, and entitled "SYSTEM AND METHOD FOR SEGMENTATION OF LUNG," which claims the benefit of and priority to U.S. Provisional Patent Application Serial No. 62/020,261 filed on Jul. 2, 2014, the entire contents of each of which are incorporated herein by reference.

BACKGROUND

Technical Field

The present disclosure relates to systems and methods for segmentation of a lung. More particularly, the present disclosure relates to systems and methods that defines the borders of the lung based on a three-dimensional (3D) model generated based on CT scan image data of a patient's chest.

Discussion of Related Art

A patient's lungs are located within a thoracic cavity, which is separated from the abdominal cavity by the muscular diaphragm located at the base of the lungs. Further, the lungs are surrounded by a double-walled sac called the pleura (visceral pleurae and parietal pleurae) and a pleural fluid between the pleura and the lungs. The pleural fluid enables the lungs to expand and contract without adhering the pleura.

Visualization techniques related to visualizing the lungs have been developed so as to help clinicians to perform diagnoses, surgeries and/or other treatment procedures. Visualization is especially important for identifying a location of a diseased region having corresponding symptoms. Further, when treating the diseased region, additional emphasis is given to identification of a correct location so that a proper procedure is performed at the correct location. Furthermore, visualization of borders of the lungs are critical because diseased regions and locations for surgical operations should be within the borders of the lungs. Thus, visualization of pleura is important because the pleura define the borders of the lungs.

SUMMARY

Provided in accordance with the present disclosure is a method for determining pleura boundaries of a lung.

In an aspect of the present disclosure, a segmentation method comprises acquiring image data from an imaging device, generating a set of two-dimensional (2D) slice images based on the acquired image data, determining, by a processor, a seed voxel in a first slice image from the set of 2D slice images, applying, by the processor, a region growing process to the first slice image from the set of 2D slice images starting with the seed voxel using a threshold value, generating, by the processor, a set of binarized 2D slice images based on the region grown from the seed voxel, filtering out, by the processor, connected components of the lung in each slice image of the set of binarized 2D slice images, and identifying, by the processor, the pleural boundaries of the lung based on the set of binarized 2D slice images.

In another aspect of the present disclosure, the seed voxel is in a portion of the first slice image from the set of binarized 2D slice images corresponding to a trachea of the lung.

In yet another aspect of the present disclosure, the threshold value is greater than or equal to an intensity of the seed voxel.

In a further aspect of the present disclosure, the acquired image data is stored in the digital imaging and communications in medicine (DICOM) image format.

In another aspect of the present disclosure, the image data is acquired via a network device.

In a further aspect of the present disclosure, applying the region growing process includes in a case where an intensity of a first voxel in the first slice image from the set of 2D slice images is lower than the predetermined threshold value and the first voxel is connected to the seed voxel, setting the intensity of the first voxel as a maximum value, and in a case where an intensity of a second voxel in the first slice image from the set of 2D slice images is not lower than the predetermined threshold value or the first voxel is not connected to the seed voxel, setting the intensity of the second voxel as a minimum value.

In another aspect of the present disclosure, the threshold value causes a high intensity area to appear around the seed voxel in the set of 2D slice images.

In a further aspect of the present disclosure, applying the region growing process further includes inversely assigning values of voxels in the set of 2D slice images, from the minimum value to the maximum value and from the maximum value to the minimum value, to obtain the set of binarized 2D slice images.

In another aspect of the present disclosure, filtering out connected components of the lung includes detecting a connected component in the set of binarized 2D slice images, calculating an area of each connected component in the set of binarized 2D slice images, determining whether the area of each connected component is less than a predetermined value, assigning the minimum value to pixels of a first connected component when it is determined that an area of the first connected component is less than the predetermined value, and assigning the maximum value to pixels of a connected component when it is determined that an area of the second connected component is greater than or equal to the predetermined value.

In a further aspect of the present disclosure, a connected component is an enclosed area with high intensity.

In another aspect of the present disclosure, the connected component is a blood vessel or an airway.

In a further aspect of the present disclosure, an intersection of three 2D slice images, each of which is from each of three independent directions, identifies a voxel in the set of 2D slice images.

In another aspect of the present disclosure, the three independent directions are axial, coronal, and sagittal directions.

In a further aspect of the present disclosure, each voxel of the set of binarized 2D slice images has either high or low intensity.

In another aspect of the present disclosure, the image data is acquired from computed tomographic technique, radiography, tomogram produced by a computerized axial tomography scan, magnetic resonance imaging, ultrasonography, contrast imaging, fluoroscopy, nuclear scans, and positron emission tomography.

In another aspect of the present disclosure, a system for determining pleura of a lung comprises an imaging device configured to image a chest of a patient to obtain image data, and an image processing device including a memory configured to store data and processor-executable instructions, and a processor configured to execute the processor-executable instructions to generate a set of two-dimensional (2D) slice images based on the acquired image data, determine a seed voxel in a first slice image from the set of 2D slice images, apply a region growing process to the first slice image from the set of 2D slice images starting with the seed voxel using a threshold value, generate a set of binarized 2D slice images based on the region grown from the seed voxel, filter out connected components of the lung in each slice image of the set of binarized 2D slice images, and identify the pleural boundaries of the lung based on the set of binarized 2D slice images.

Any of the above aspects and embodiments of the present disclosure may be combined without departing from the scope of the present disclosure.

BRIEF DESCRIPTION OF THE DRAWINGS

Objects and features of the presently disclosed systems and methods will become apparent to those of ordinary skill in the art when descriptions of various embodiments are read with reference to the accompanying drawings, of which.

DETAILED DESCRIPTION

The present disclosure is related to systems and methods for segmenting image data of a patient's chest to identify the pleural boundaries of the patient's lungs.

Segmenting image data of a patient's chest to identify the pleural boundaries of the patient's lungs may be a necessary component of an ELECTROMAGNETIC NAVIGATION BRONCHOSCOPY® (ENB) procedure using an electromagnetic navigation (EMN) system. An ENB procedure generally involves at least two phases: (1) planning a pathway to a target located within, or adjacent to, the patient's lungs; and (2) navigating a probe to the target along the planned pathway. An example of the planning software described herein can be found in U.S. patent application Ser. Nos. 13/838,805, 13/838,997, and 13/839,224, all of which are filed by Covidien LP on Mar. 15, 2013 and entitled "Pathway Planning System and Method," all of which are incorporated herein by reference. An example of the planning software can be found in commonly assigned U.S. Provision Patent Application No. 62/020,240 entitled "SYSTEM AND METHOD FOR NAVIGATING WITHIN THE LUNG" the entire contents of which are incorporated herein by reference.

Prior to the planning phase, the patient's lungs are imaged by, for example, a computed tomography (CT) scan, although additional applicable methods of imaging will be known to those skilled in the art. The image data assembled during the CT scan may then be stored in, for example, the Digital Imaging and Communications in Medicine (DICOM) format, although additional applicable formats will be known to those skilled in the art. The CT scan image data may then be loaded into a planning software application ("application") to be processed for generating a 3D model which may be used during the planning phase of the ENB procedure. Segmenting image data of the patient's chest may be a component of the process of generating the 3D model, or may be performed separately.

The application may use the CT scan image data to generate a 3D model of the patient's lungs. The 3D model may include, among other things, a model airway tree corresponding to the actual airways of the patient's lungs, and showing the various passages, branches, and bifurcations of the patient's actual airway tree. While the CT scan image data may have gaps, omissions, and/or other imperfections included in the image data, the 3D model is a smooth representation of the patient's airways, with any such gaps, omissions, and/or imperfections in the CT scan image data filled in or corrected. After it is generated, the 3D model may be presented in various views. Although the present disclosure will be described in terms of specific illustrative embodiments, it will be readily apparent to those skilled in this art that various modifications, rearrangements and substitutions may be made without departing from the spirit of the present disclosure. The scope of the present disclosure is defined by the claims appended hereto.

Figure 1:
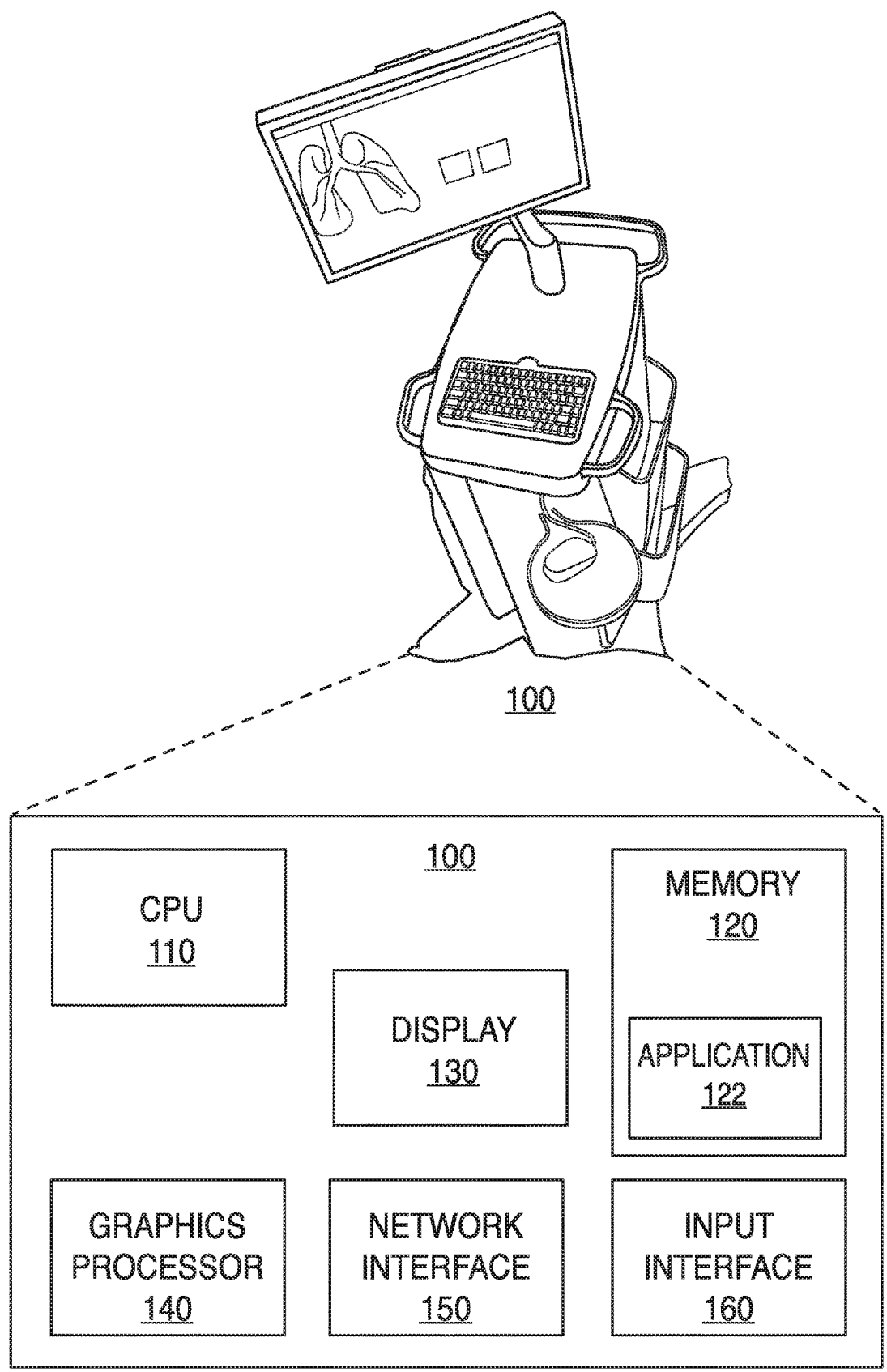
FIG. 1 is a schematic diagram of an example device which may be used for segmenting computed tomography (CT) image data of a patient's lungs, in accordance with an embodiment of the present disclosure.

FIG. 1 shows an image processing device 100 that may be used for segmentation of the lungs. Device 100 may be a specialized image processing computer configured to perform the functions described below. Device 100 may be embodied in any form factor known to those skilled in the art, such as, a laptop, desktop, tablet, or other similar computer. Device 100 may include, among other things, one or more processors 110, memory 120 storing, among other things, the above-referenced application 122, a display 130, one or more specialized graphics processors 140, a network interface 150, and one or more input interfaces 160.

The CT scan image data may be stored in the memory 120 in the DICOM format. A set of 2D slice images may be generated based on the CT scan image data. In an aspect, the 2D slice images may be generated to depict the axial, coronal, and sagittal views of the patient at a given location. For example, at each intersecting point of the chest, there may be three different 2D slice images generated in the three independent directions. These 2D slice images may be loaded into application 122 which is executed by processors 110 to reformat the 2D slice images for display. For example, application 122 may convert a color space of the 2D slice images to another color space suitable for display and perform imaging processes, e.g., scale, rotation, translation, or projection, to display the 2D slice images as intended. Based on at least three different 2D slice images, a voxel may be identified. The 2D slice images may be processed using a region growing algorithm to distinguish different types of tissue and materials to identify the pleural boundaries of the lungs. A variety of region growing algorithms are known in the art. Memory 120 may also store applications that may generate the 3D model of the chest or that may identify the pleural boundaries of the lungs.

FIG. 2 illustrates three 2D slice images identifying a seed voxel 220, which is identified as a pixel from each 2D slice image (205, 210, 215) which define the voxel for segmentation in accordance with an embodiment of the present disclosure. As shown in FIG. 2, seed voxel 220 is identified at an intersecting point in the trachea of a patient where the three 2D slice images intersect with each other. Segmentation is an image processing step that partitions the set of 2D slice images based on a Hounsfield value assigned to a voxel in the set of 2D slice images, and is used for defining difference in the intensity of the images in order to more clearly define organs and other varying intensity aspects of the images and, in embodiments of the present disclosure, the pleural boundaries of the lungs.

In one embodiment, segmentation may be used to distinguish an inside area of the lungs from an outside area of the lungs in the set of 2D slice images. Segmentation may include binarization where the 2D slice images are displayed with only two different intensity values, and filtering processes as will be described in greater detail below.

Figure 2A:
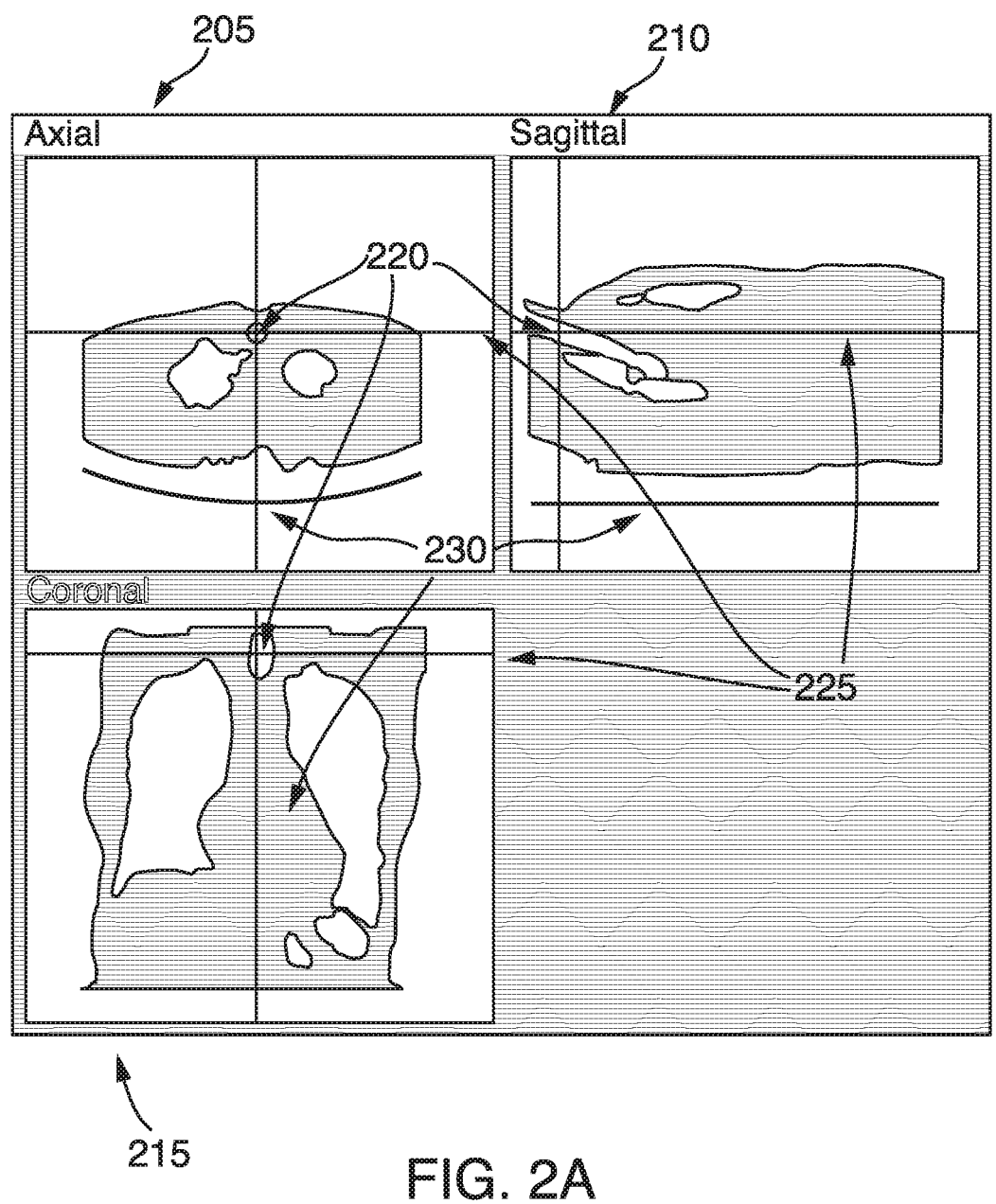
FIG. 2A is a graphical illustration of 2D images identifying a voxel for segmentation with the lung area shown in black, in accordance with an embodiment of the present disclosure.

As a first step of the present disclosure, a set of 2D slice images is generated from CT scan image data of the patient's chest. Once the set of 2D slice images is generated, a seed voxel 220 must be selected. FIG. 2A depicts a manual process whereby the seed voxel 220 is shown being selected in the 2D slice images. Three 2D slice images 205, 210, and 215 depict the chest of a patient along each of the axial, sagittal, and coronal directions, and identify the starting seed voxel 220. To better illustrate the starting seed voxel 220, the horizontal axis 225 and the vertical axis 230 are displayed in each of the three 2D slice images 205, 210, and 215. The intersection of the horizontal axis 225 and the vertical axis 230 is the starting seed voxel 220. In an aspect, the starting seed voxel 220 may be inside of the lung or a trachea and may be determined manually or automatically. By selecting a seed voxel 220 in the trachea the as the seed voxel 220, processes can be undertaken to quickly identify the airways within the lung from tissues outside of the lungs.

The trachea has a substantially constant diameter along its length. In particular, the upper part of the trachea extends substantially linearly from the larynx and pharynx and behind the sternum. By using these properties of the trachea, the trachea may be found in the 2D slice images. Further details of finding the trachea to determine the starting seed voxel 220 is described in commonly assigned U.S. Provisional Patent Application No. 62/020,253 entitled "Trachea Marking", filed on Jul. 2, 2014 by Lachmanovich et al.; and U.S. Provisional Patent Application No. 62/020,257 entitled "Automatic Detection Of Human Lung Trachea", filed on Jul. 2, 2014 by Markov et al.

After the starting seed voxel 220 is selected either manually or automatically, a region growing algorithm is used to binarize the 2D slice images. Based on the region growing algorithm, every voxel in the set of 2D slice images is checked to determine whether a Hounsfield value assigned to each voxel is less than a threshold value and whether each voxel is connected to the starting voxel 220. When it is determined that a value assigned to a voxel has a Hounsfield value less than the threshold value and is connected to the starting seed voxel 220, the Hounsfield value of the voxel is set to one or the maximum value. Otherwise, the Hounsfield value of the voxel is set to zero or the minimum value. As part of the region growing algorithm, the threshold is selected with a high enough value to cause leakage in the lung, and thus fill the lungs with intensity values leaked from the airways.

Figure 2B:
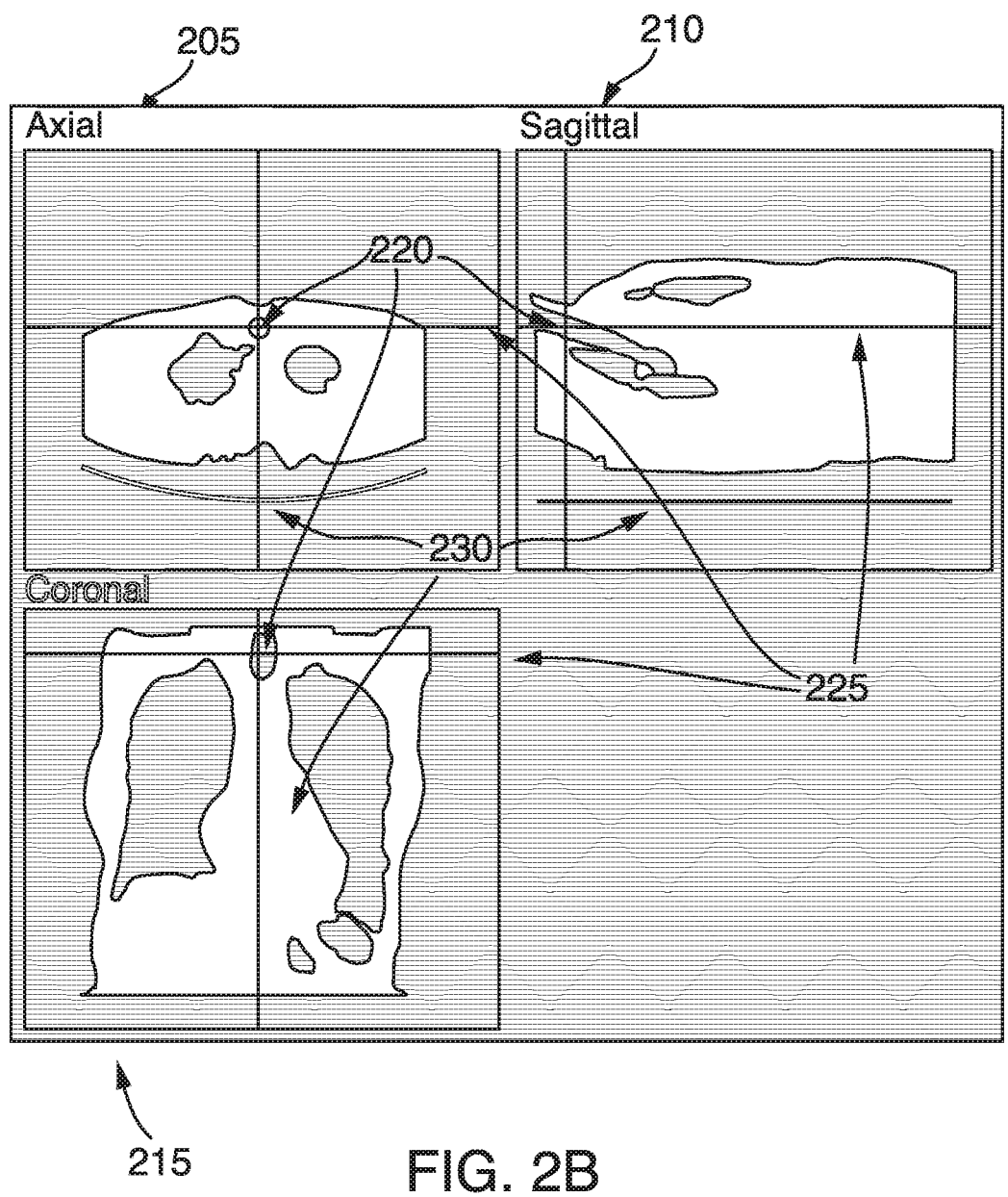
FIG. 2B is a graphical illustration of 2D images identifying a voxel for segmentation with the lung area shown in white, in accordance with an embodiment of the present disclosure.

After every voxel in the set of 2D slice images is set to the maximum or minimum value, the 2D slice images will have only 2 colors of pixels. The result is a set of 2D slice images where the voxels/pixels having the maximum Hounsfield value would appear white, and the voxels/pixels having the minimum Hounsfield value would appear black. As shown in FIG. 2B, in some instances, the values of voxels in the set of 2D slice images, and thus the pixels in the 2D slice images, are inversed so that the lung regions are shown in black and the non-lung regions are shown in white or another color.

Figure 3:
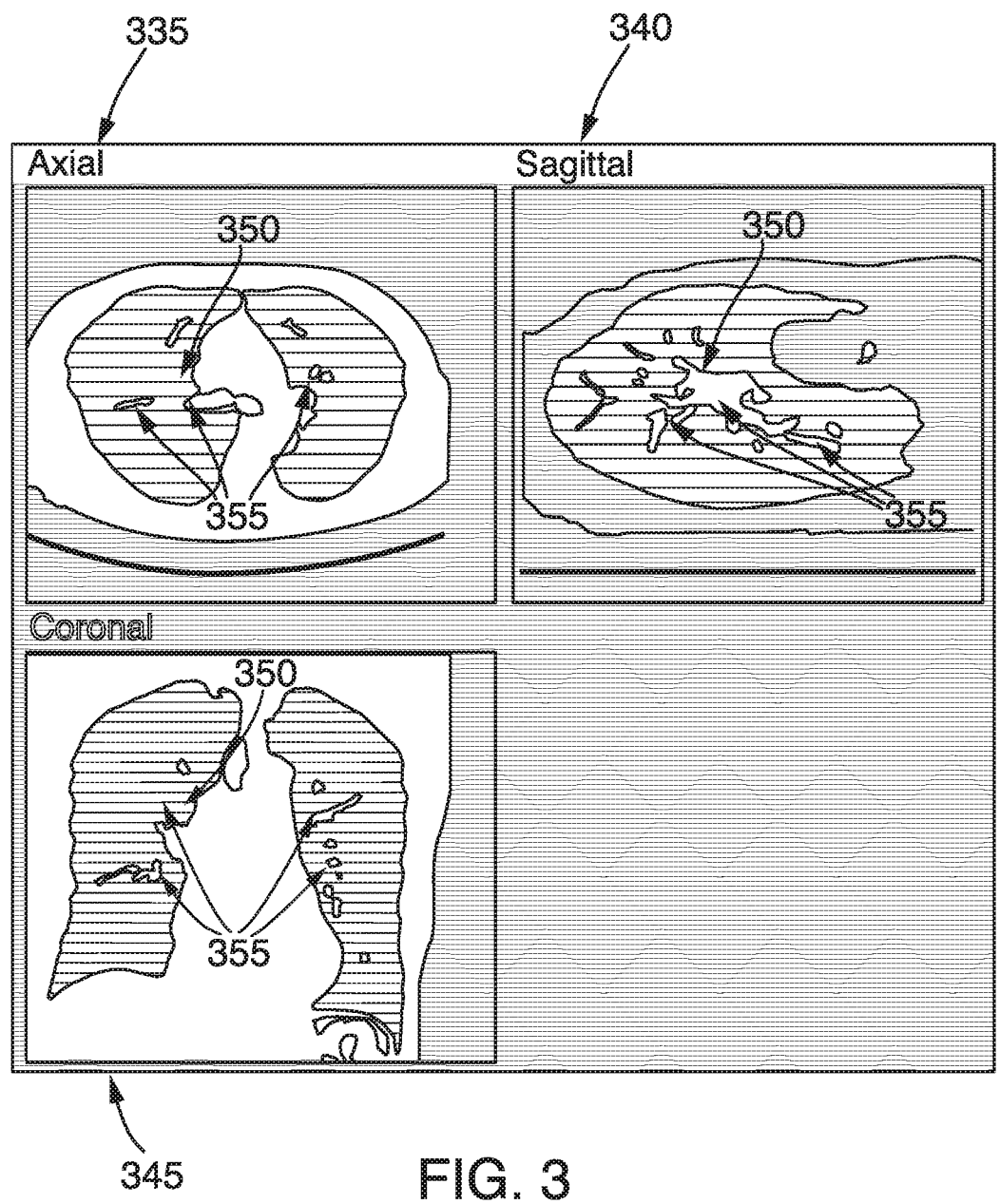
FIG. 3 is a graphical illustration of 2D images identifying a voxel for segmentation with the lung area shown in grey, in accordance with an embodiment of the present disclosure.

FIG. 3 shows three 2D slice images 335, 340, and 345 depicting the results of the segmentation and binarization with the lung tissue clearly depicted in grey on a background of the chest and other non-airway or lung tissues in white. Though not yet complete, the views of FIG. 3 substantially identify the pleural boundaries of the lungs.

Since the lung has a porous structure, most of voxels of the binarized set of 2D slice images representing the lung and the airways are shown in black. Some airway tissue (e.g., 355 in FIG. 3) having a Hounsfield value greater than the threshold, however, will be shown in white. Further, voxels of the binarized 3D volume outside of the lung may also be shown in white because they are not connected to the starting seed voxel 220 and have the maximum intensity value. Indeed any tissue having a Hounsfield value above the threshold (e.g., voxel 350), will be shown as white.

The segmented, binarized, and inversed set of 2D slice images may contain large black regions, which cover the lung. In an aspect, the threshold value may be adjusted to make the large black regions as large as possible to cover the pleural boundaries of the lungs with sufficient accuracy. By decreasing the threshold value, voxels representing walls of small airways or blood vessels appear in white and at the same time, the large black regions become smaller. On the other hand, when the threshold value is increased, the walls of small airways and blood vessels may not appear in white and the large black regions become larger. Thus, the threshold values may be adjusted to a value so that walls of airways and blood vessels, having a certain size, appear in in white and so that the large black regions grow as large as the pleura of the lungs.

Figure 4A:
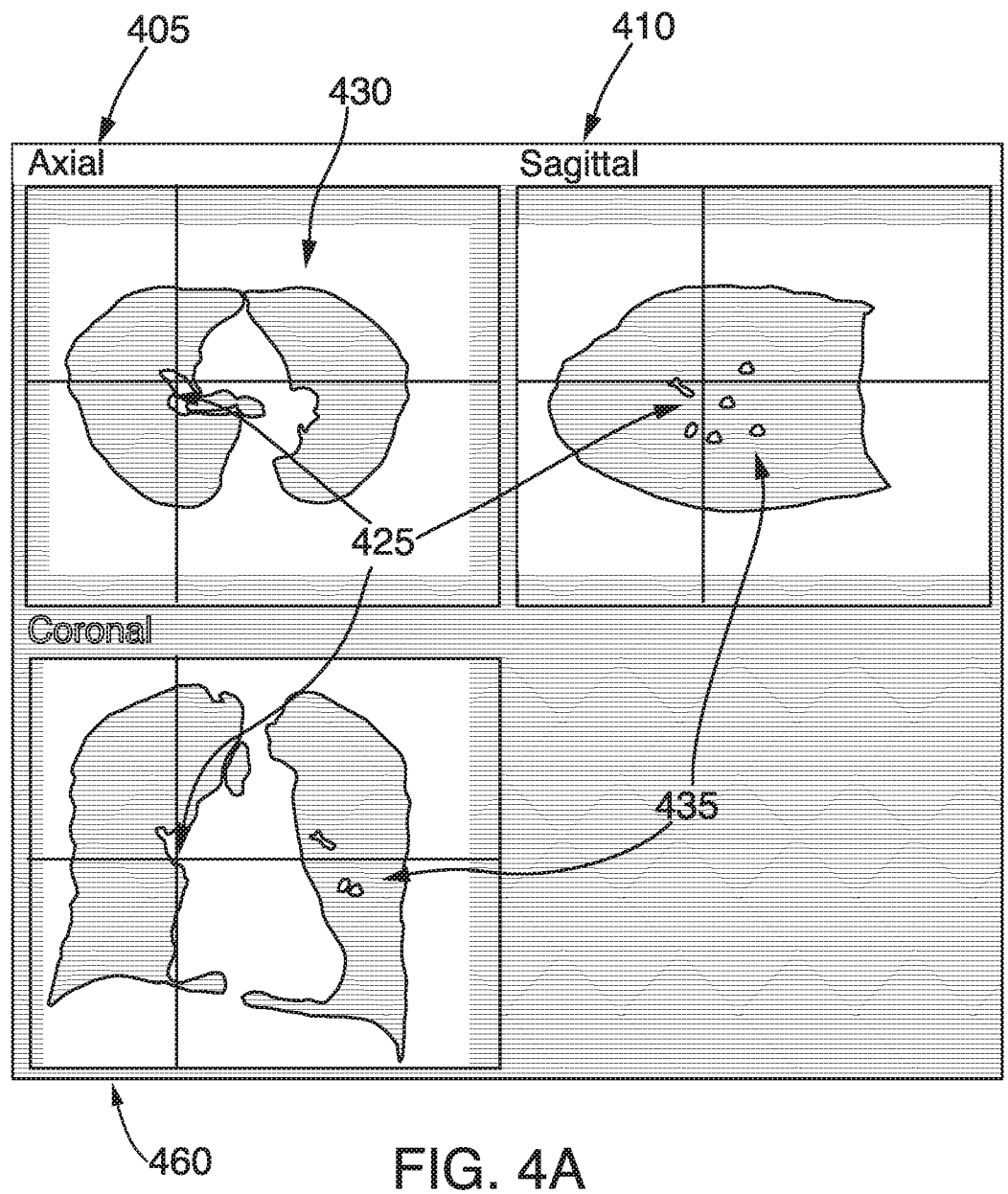
FIGS. 4A-4B are graphical illustrations of a filtering process of connected components in 2D images of a patient's lungs, in accordance with an embodiment of the present disclosure.
Figure 4B:
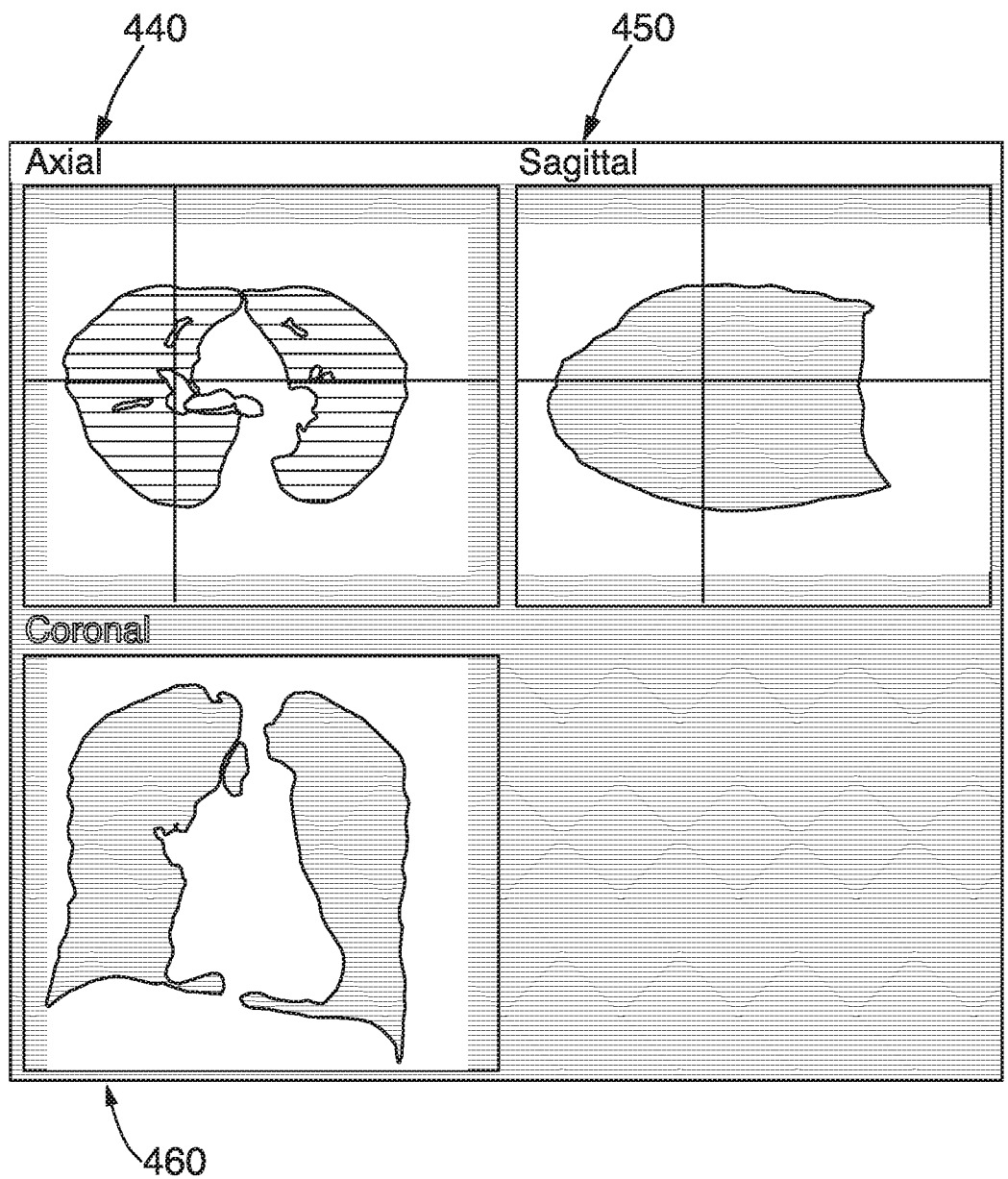

The binarized, segmented and inversed set of 2D slice images may be viewed in the axial, coronal, and sagittal directions. FIGS. 4A and 4B shows binarized 2D slice images for filtering out connected components, as well as filtered out 2D slice images, in accordance with an embodiment of the present disclosure. The three 2D slice images 405, 410, and 415 are black and white images. The black region 420 represents the lung, while white region represents areas outside of the lung and also some connected components, such as blood vessels and walls of airways, in the lung. These connected components are shown as small white areas 435 in the 2D slice images 410 and 415.

Filtering out connected components starts from detecting connected components in each 2D slice image. Connected components are displayed as white regions in the large black regions, which represent the lung. When the connected components are detected, an area of each connected component is calculated. In a case where a calculated area is less than a threshold value, the corresponding connected component is filtered out, meaning that pixels in the corresponding connected component are reassigned to zero. In other words, the corresponding connected component is merged into the lung area or the large black regions. After all connected components in the 2D slice image have been filtered out, a filtered out 2D slice image 405 along the axial direction is obtained. The filtered out 2D slice image 405 includes large black regions 420, whose boundaries define the pleural boundary of the lungs.

FIG. 4B includes filtered out 2D slice images 440, 450, and 460 along the axial, coronal, and sagittal directions, respectively. After filtering out connected components in all the 2D slice images, each filtered out 2D slice image has large black regions as shown in the filtered out 2D slice images 440, 450, and 460. These filtered out 2D slice images are reassembled to generate a segmented set of 2D slice images, which includes black regions defining the pleural boundaries of the lungs. These black regions also define or restrict spaces for diagnosis of and/or surgeries to the lungs. This pleural boundary defining set of 2D slice images may be incorporated into pathway planning and treatment software such as the iLogic software sold by Covidien LP for diagnosis and treatment of the lungs of a patient. The clear definition of the pleural boundaries can be used to partition the lungs from the surrounding tissue, and thereby used to create the 3D volume of the patient's lungs.

Figure 5A:
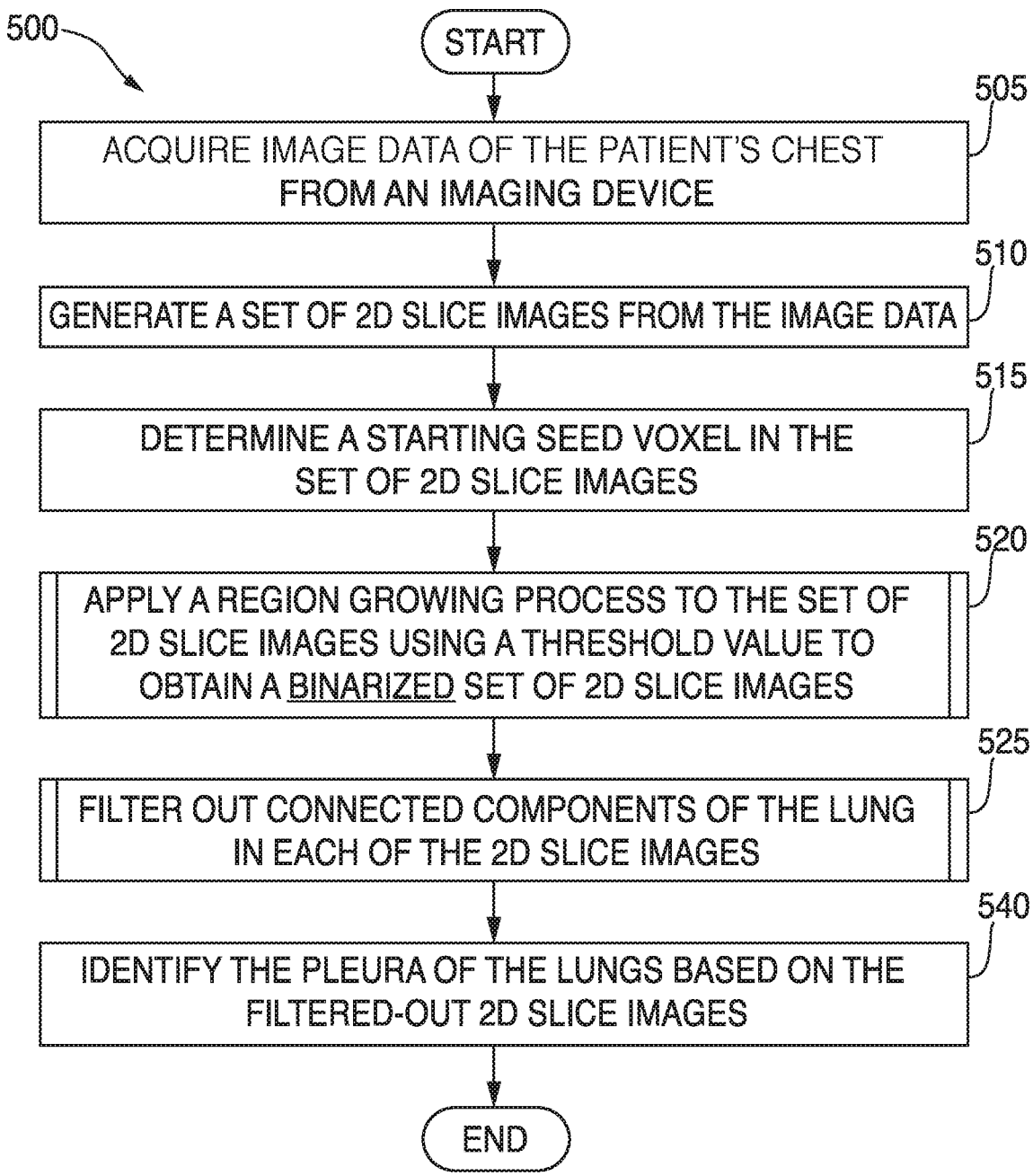
FIG. 5A is a flowchart illustrating an example method for segmenting 2D images of a patient's lungs to define the pleura boundary of patient's lungs, in accordance with an embodiment of the present disclosure.
Figure 5B:
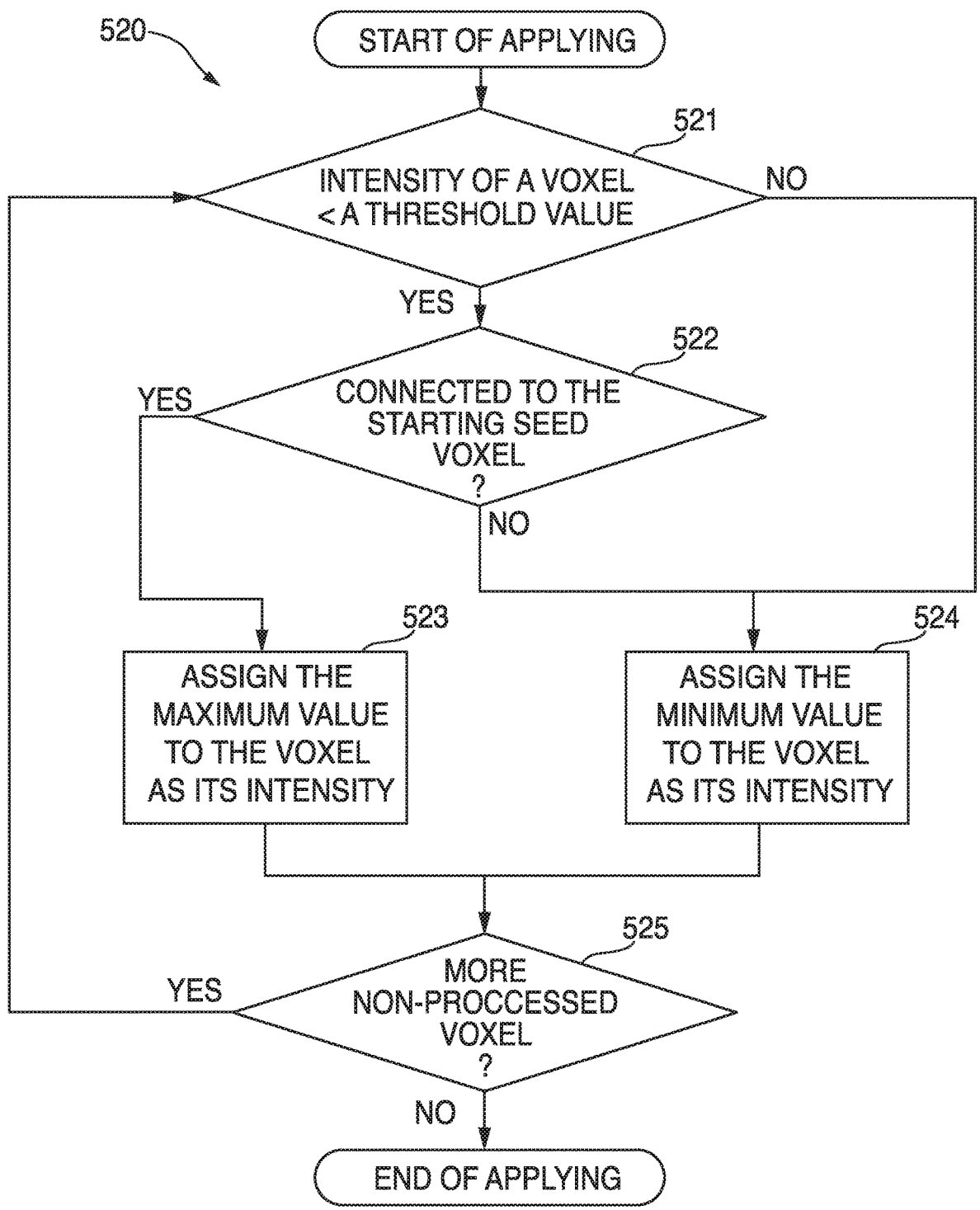
FIG. 5B is a flowchart illustrating an example method for applying a region growing process, in accordance with an embodiment of the present disclosure.
Figure 5C:
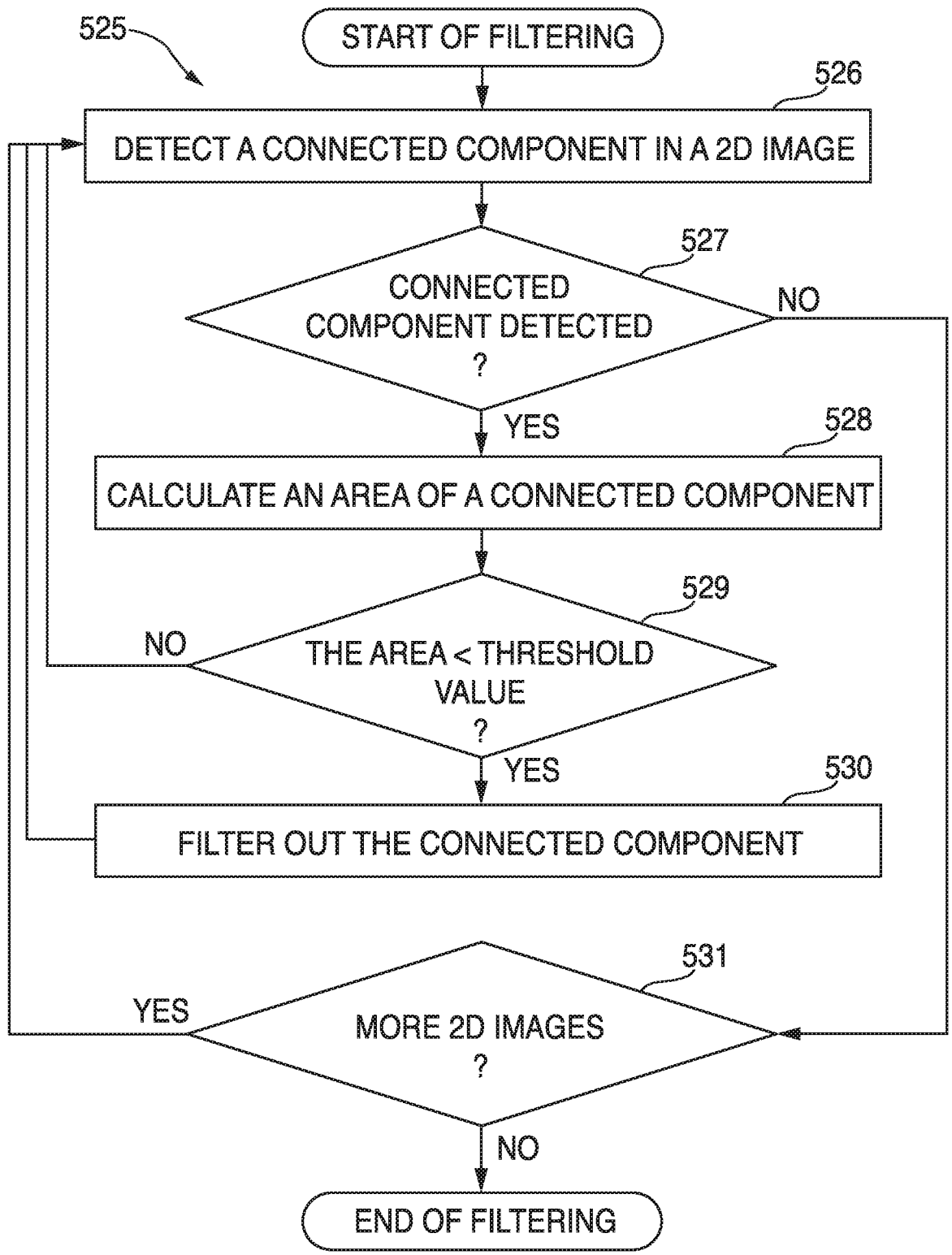
FIG. 5C is a flowchart illustrating an example method for filtering out connected components, in accordance with an embodiment of the present disclosure.

FIGS. 5A-5C show flowcharts of a segmentation method 500 for generating a segmented set of 2D slice images defining the pleural boundaries of a lung, in accordance with an embodiment of the present disclosure. The segmentation method 500 starts from step 505, in which CT scan image data of the chest of a patient is obtained, for example from a CT scanner. In an aspect, the CT image data may be obtained from another imaging modality, such as radiography, tomogram produced by a CAT scan, MRI, ultrasonography, contrast imaging, fluoroscopy, nuclear scans, and PET.

In step 510, the CT scan image data is processed to generate a set of 2D slice images of the patient's chest. The set of 2D slice images may include the lung, the pleura, the trachea, the heart, the stomach, and any other organs in the chest. A voxel is defined as the intersection of three 2D slice images viewed in the three directions, e.g., the axial, sagittal, and coronal directions. Each voxel has a value representing three pixels, each of which is from a corresponding 2D slice image among the three 2D slice images viewed in the three directions. Segmentation of the set of 2D slice images of the chest starts by determining a seed voxel 220 in the set of 2D slice images, and distinguishes a region including the starting seed voxel from an area not including the starting seed voxel. In step 515, the starting seed voxel is determined automatically or manually. The starting seed voxel may be located at an inside area of the trachea or of the lung. When the trachea is used to determine the starting seed voxel, methods for automatically finding a trachea can be found in commonly assigned U.S. Provisional Patent Application No. 62/020,253 entitled "Trachea Marking", filed on Jul. 2, 2014 by Lachmanovich et al.; and U.S. Provisional Patent Application No. 62/020,261 entitled "Automatic Detection Of Human Lung Trachea", filed on Jul. 2, 2014 by Markov et al., the entire contents of both of which is incorporated by reference. After finding the trachea, any voxel inside of the trachea may be determined as the starting seed voxel.

In step 520, a region growing algorithm is applied to process the set of 2D slice images. The region growing algorithm is used to connect more voxels to the seed voxel to grow the region containing the starting seed voxel. This region may be used to determine the borders of the lung at the end of the segmentation method 500.

By applying the region growing algorithm, each voxel of the set of 2D slice images is binarized, that is, it has its Hounsfield value compared to a threshold and reassigned to two colors, black and white. Black voxels represent the lung region and white voxels represent the non-lung region. After the step 520, a new binarized set of 2D slice images is generated. Details of the step 520 is further described with reference to FIG. 5B below.

In step 525, all 2D slice images are processed to filter out connected components therein. Connected components may represent blood vessels and walls of airways having a Hounsfield value greater than the threshold identified above. Connected components are displayed as white areas within the lung area in 2D slice images. By filtering out or removing the white areas having a size smaller than a predetermined threshold from within the lung area, an area covering the lung may be displayed only in black and the 2D slice images are prepared for determining the pleural boundaries of the lungs. Detailed descriptions for the filtering out process are provided with reference to FIG. 5C below.

After the filtering out process, in step 540, the processed set of 2D slice images may be used to identify the pleural boundaries of the lungs. The segmentation method is ended after step 540. By performing the binarization and connected component analysis on the 2D slice images with a minimum size limitation, the true boundaries, particularly the pleural boundaries are clearly defined for the clinician. Alternatively, instead of using the original CT scan image data, the 2D slice images used for process 500 may be generated from a different dataset. An example of another potential dataset to be used for process 500 is a set of 2D slice images generated based on a 3D model which was generated based on the original CT scan image data. Such a 3D model may present a smoother view of the patient's lungs with any gaps, omissions, and/or imperfections in the CT scan image data filled in or corrected. FIG. 5B shows a flowchart illustrating step 520 of FIG. 5A, i.e., applying the region growing algorithm to voxels of the set of 2D slice images of the patient's chest. In step 521, an intensity (Hounsfield value) of a voxel of the set of 2D slice images is compared with a threshold value.

When it is determined that the intensity of the voxel is greater than or equal to the threshold value, step 524 follows, and otherwise step 522 follows. In step 522, connectedness between the voxel and the starting seed voxel is determined. Here, connectedness ensures that the voxel is in the same region as the starting seed voxel, or in other words, the voxel is in the lung region. This is done by considering the surrounding voxels and determining whether they satisfy the same threshold criteria. This process is continued back to the starting seed voxel. Stated another way, when there is a pathway from the voxel to the starting seed voxel and the pathway is made up of a series of adjacent voxels satisfying the threshold criteria, then the voxel is considered connected to the starting seed voxel. When it is determined that the voxel is connected to the starting seed voxel, the intensity value of the voxel is assigned to the maximum value in step 523. The result is a binary mask of voxel intensities, with all connected voxels satisfying the threshold criteria having one assigned intensity value and all others having another intensity value.

In an aspect, voxels, which are considered as seed voxel candidates, directly adjacent to a seed voxel may be compared with the threshold value recursively without considering connectedness. This recursion method starts by comparing voxels adjacent to the starting seed voxel and recursively proceeds in all directions. In this case, checking for connectedness is unnecessary.

When it is determined that the intensity of the voxel is not less than the threshold value in step 521, or that the voxel is not connected to the starting seed point in step 522, the intensity of the voxel is assigned to the minimum value in step 523. In steps 523 and 524, the set of 2D slice images are segmented, resulting in voxels having only the minimum value or the maximum value.

Step 525 follows after the steps 523 and 524. In step 525, it is determined whether there remain voxels which have not been processed through the region growing algorithm. When there is such a voxel, steps 521-525 are repeated until there are no more unprocessed voxels. The result of steps 521-525 is a binarized set of 2D slice images which only includes black voxels for non-lung regions and white voxels for lung regions. In step 526, the assigned value of each voxel is inversed from the maximum to the minimum or from the minimum to the maximum so that the lung regions have black voxels and the non-lung regions have white voxels. In an aspect, the threshold value used in step 521 may be adjusted to cause sufficient leakage (e.g., a high intensity region) in the lung region such that the high intensity region may cover the lung and the borders of the lung. In another aspect, the threshold value is greater than or equal to the intensity value of the seed voxel.

FIG. 5C shows a flowchart for step 525 of FIG. 5A, i.e., filtering out connected components from the 2D slice images, in accordance with an embodiment of the present disclosure. Step 525 starts from step 526, i.e., detecting a connected component in a 2D slice image generated from the binarized set of 2D slice images. The connected component may represent a blood vessel and/or a wall of airways. In step 527, it is determined whether a connected component is detected. If it is determined that the connected component is not detected in step 527, the filtering out step 525 goes to step 531 to check whether there are more 2D slice images to detect connected components.

When it is determined that a connected component is detected in step 527, an area of the detected connected component is calculated in step 528. The area may be a number of pixels in a white area representing the connected component.

In step 529, the calculated area is compared with a threshold value. When it is determined that the calculated area is greater than or equal to the threshold value, it goes back to step 526. That means the connected components may not be a blood vessel or a wall of airways. When it is determined that the calculated area is less than the threshold value, in step 530, the connected component is filtered out or removed. In other words, pixels in the connected components are assigned to the minimum value. In result, the connected component is merged into the large black regions covering the lung and the pleura.

In step 531, it is determined whether there are more 2D slice images to be processed. When it is determined that there is an unprocessed 2D image, steps 526-530 are repeated to filter out connected components in the unprocessed 2D slice image. Otherwise, the filtering out step 525 is complete.

In an aspect, the filtering out step 540 may process 2D slice images taken along one direction and process 2D slice images taken along another direction. For example, step 540 processes 2D slice images taken along the axial direction first and other 2D slice images taken along the coronal direction and the sagittal direction in order. In another aspect, step 540 may process 2D slice images one by one without any order.

By binarizing the set of 2D slice images and filtering out connected components in the 2D slice images, the resulting set of 2D slice images, which is the segmented set of 2D slice images, may be used to determine the pleural boundaries of the lungs, which may be used during either the planning or navigation phases of an ENB procedure. For example, this information may be useful during a planning phase to identify when a suspected target is located outside of the lungs. Alternatively, during a procedure, this information can be used to notify the clinician when a tool is approaching the pleural boundaries. In both instances awareness of the location of the pleural boundaries assists the clinician in avoiding complications such a pneumothorax and other conditions which may occur as the clinician considers or approaches targets at or near the boundaries of the lungs.

Returning now to FIG. 1, memory 120 includes application 122 such as EMN planning and procedure software and other data that may be executed by processors 110. For example, the data may be the CT scan image data stored in the DICOM format and/or the 3D model generated based on the CT scan image data. Memory 120 may also store other related data, such as medical records of the patient, prescriptions and/or a disease history of the patient. Memory 120 may be one or more solid-state storage devices, flash memory chips, mass storages, tape drives, or any computer-readable storage media which are connected to a processor through a storage controller and a communications bus. Computer readable storage media include non-transitory, volatile and non-volatile, removable and non-removable media implemented in any method or technology for storage of information such as computer-readable instructions, data structures, program modules or other data. For example, computer-readable storage media includes random access memory (RAM), read-only memory (ROM), erasable programmable read only memory (EPROM), electrically erasable programmable read only memory (EEPROM), flash memory or other solid state memory technology, CD-ROM, DVD or other optical storage, magnetic cassettes, magnetic tape, magnetic disk storage or other magnetic storage devices, or any other medium which can be used to store desired information and which can be accessed by device 100.

Display 130 may be touch-sensitive and/or voice-activated, enabling display 130 to serve as both an input device and an output device. Graphics processors 140 may be specialized graphics processors which perform image-processing functions, such as processing the CT scan image data to generate the 3D model, and process the 3D model to generate the 2D slice images of the 3D model in the various orientations as described above, as well as the 3D renderings of the 3D model. Graphics processors 140 may further be configured to generate a graphical user interface (GUI) to be displayed on display 130. The GUI may include views showing the 2D image slices, the 3D rendering, among other things. In embodiments, graphics processors 140 may be specialized graphics processors, such as a dedicated graphics processing unit (GPU), which performs only the image processing functions so that the one or more general processors 110 may be available for other functions. The specialized GPU may be a stand-alone dedicated graphics card, or an integrated graphics card.

Network interface 150 enables device 100 to communicate with other devices through a wired and/or wireless network connection. In an embodiment, device 100 may receive the CT scan image data from an imaging device via a network connection. In other embodiments, device 100 may receive the CT scan image data via a storage device, such as a disk or other external storage media known to those skilled in the art.

Input interface 160 is used for inputting data or control information, such as setting values, text information, and/or controlling device 100. Input interface 160 may include a keyboard, mouse, touch sensor, camera, microphone, or other data input devices or sensors used for user interaction known to those skilled in the art.

In addition, reference is made to following commonly assigned applications: U.S. Provisional Patent Application Ser. No. 62/020,220 entitled "Real-Time Automatic Registration Feedback", filed on Jul. 2, 2014, by Brown et al.; U.S. Provisional Patent Application Ser. No. 62/020,242 entitled "Unified Coordinate System for Multiple CT Scans of Patient Lungs", filed on Jul. 2, 2014, by Greenburg.; U.S. Provisional Patent Application Ser. No. 62/020,245 entitled "Alignment CT", filed on Jul. 2, 2014, by Klein et al.; U.S. Provisional Patent Application Ser. No. 62/020,250 entitled "Algorithm for Fluoroscopic Pose Estimation", filed on Jul. 2, 2014, by Merlet.; U.S. Provisional Patent Application Ser. No. 62/020,258 entitled "Cone View—A Method of Providing Distance and Orientation Feedback While Navigating in 3D", filed on Jul. 2, 2014, by Lachmanovich et al.; and U.S. Provisional Patent Application Ser. No. 62/020,262 entitled "Dynamic 3D Lung Map View for Tool Navigation Inside the Lung", filed on Jul. 2, 2014, by Weingarten et al., the entire contents of all of which are hereby incorporated by reference. All of these references are directed to aspects of modifying and manipulating the DICOM images to provide enhanced clarity and performance for analysis, diagnostic, and treatment systems relating to, among other things, lung treatment planning and navigation.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method for determining pleural boundaries of a lung, comprising:
    applying, by a processor, a region growing process to a first slice image of a set of 2D slice images to form a grown region, the region growing process starting with a seed voxel within a trachea and using a threshold value, wherein the region growing process includes:
        in a case where an intensity of a first voxel in a first slice image from the set of 2D slice images is lower than the threshold value and the first voxel is connected to the seed voxel, setting the intensity of the first voxel as a maximum value; and
        in a case where an intensity of a second voxel in the first slice image from the set of 2D slice images is not lower than the threshold value or the first voxel is not connected to the seed voxel, setting the intensity of the second voxel as a minimum value;
    filtering out, by the processor, connected components of a lung in each slice image of a set of binarized 2D slice images generated from the grown region; and
    identifying, by the processor, the pleural boundary of the lung based on the set of binarized 2D slice images.

2. The method according to claim 1, wherein the threshold value is greater than or equal to an intensity of the seed voxel.

3. The method according to claim 1, wherein the set of 2D slice images is stored in digital imaging and communications in medicine (DICOM) image format.

4. The method according to claim 1, further comprising:
    acquiring image data of a patient's chest;
    generating the set of 2D slice images based on the acquired image data; and
    determining the seed voxel in the trachea connected to the lung in the first slice image of the set of 2D slice images.

5. The method according to claim 1, wherein the threshold value causes a high intensity area to appear around the seed voxel in the set of 2D slice images.

6. The method according to claim 5, wherein applying the region growing process further includes inversely assigning values of voxels in the set of 2D slice images, from the minimum value to the maximum value and from the maximum value to the minimum value, to obtain the set of binarized 2D slice images.

7. The method according to claim 1, wherein filtering out connected components of the lung includes:
    detecting a plurality of connected components in the set of binarized 2D slice images;
    calculating an area of each connected component in the set of binarized 2D slice images;
    determining whether the area of each connected component is less than a predetermined value;
    assigning a minimum value to pixels of a first connected component of the plurality of connected components when it is determined that an area of the first connected component is less than the predetermined value; and
    assigning a maximum value to pixels of a second connected component of the plurality of connected components when it is determined that an area of the second connected component is greater than or equal to the predetermined value.

8. The method according to claim 7, wherein each connected component is an enclosed area with high intensity.

9. The method according to claim 7, wherein one or more of the plurality of connected components are blood vessels or airways.

10. The method according to claim 7, wherein an intersection of three 2D slice images, each of which is from each of three independent directions, identifies a voxel in the set of 2D slice images.

11. The method according to claim 10, wherein the three independent directions are axial, coronal, and sagittal directions.

12. The method according to claim 1, wherein each voxel of the set of binarized 2D slice images has either high or low intensity.

13. The method according to claim 1, wherein the set of 2D slice images is acquired from one of computed tomographic technique, radiography, tomogram produced by a computerized axial tomography scan, magnetic resonance imaging, ultrasonography, contrast imaging, fluoroscopy, nuclear scans, and positron emission tomography.

* * * * *